United States Patent
Dogdas et al.

(10) Patent No.: US 11,182,900 B2
(45) Date of Patent: Nov. 23, 2021

(54) SYSTEMS AND METHODS FOR PROCESSING ELECTRONIC IMAGES FOR BIOMARKER LOCALIZATION

(71) Applicant: PAIGE.AI, Inc., New York, NY (US)

(72) Inventors: Belma Dogdas, Ridgewood, NJ (US); Christopher Kanan, Rochester, NY (US); Thomas Fuchs, New York, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/160,127

(22) Filed: Jan. 27, 2021

(65) Prior Publication Data

US 2021/0233236 A1 Jul. 29, 2021

Related U.S. Application Data

(60) Provisional application No. 62/966,723, filed on Jan. 28, 2020.

(51) Int. Cl.
*G06T 7/00* (2017.01)
*G16H 10/40* (2018.01)

(52) U.S. Cl.
CPC ........... *G06T 7/0012* (2013.01); *G16H 10/40* (2018.01); *G06T 2207/20081* (2013.01);
(Continued)

(58) Field of Classification Search
CPC ......... G06T 7/0012; G06T 2207/30096; G06T 2207/20084; G06T 2207/20081; G06T 2207/30024; G16H 10/40
See application file for complete search history.

(56) References Cited

U.S. PATENT DOCUMENTS

2016/0123964 A1* 5/2016 Tumeh ............... C07K 16/2818
424/133.1
2019/0113423 A1* 4/2019 Goodman ............. G06T 7/0014
(Continued)

FOREIGN PATENT DOCUMENTS

WO 2018065434 A1 4/2018
WO 2018165103 A1 9/2018

OTHER PUBLICATIONS

International Search Report and Written Opinion dated Apr. 9, 2021 in counterpart International Patent Application No. PCT/US2021/015323 (12 pages, in English).
(Continued)

*Primary Examiner* — Jon Chang
(74) *Attorney, Agent, or Firm* — Bookoff McAndrews, PLLC

(57) ABSTRACT

Systems and methods are disclosed for receiving digital images of a pathology specimen from a patient, the pathology specimen comprising tumor tissue, the one or more digital images being associated with data about a plurality of biomarkers in the tumor tissue and data about a surrounding invasive margin around the tumor tissue; identifying the tumor tissue and the surrounding invasive margin region to be analyzed for each of the one or more digital images; generating, using a machine learning model on the one or more digital images, at least one inference of a presence of the plurality of biomarkers in the tumor tissue and the surrounding invasive margin region; determining a spatial relationship of each of the plurality of biomarkers identified in the tumor tissue and the surrounding invasive margin region to themselves and to other cell types; and determining a prediction for a treatment outcome and/or at least one treatment recommendation for the patient.

19 Claims, 13 Drawing Sheets

(52) U.S. Cl.
CPC ............... *G06T 2207/20084* (2013.01); *G06T 2207/30024* (2013.01); *G06T 2207/30096* (2013.01)

(56) References Cited

U.S. PATENT DOCUMENTS

2019/0295252 A1    9/2019   Fuchs et al.
2020/0226462 A1*   7/2020   Maddison .......... G06K 9/00134

OTHER PUBLICATIONS

Komura, Daisuke, el al. "Machine learning methods for histopathological image analysis" Computational and structural biotechnology journal 16 (2018): 34-42. (9 pages, in English).

* cited by examiner

SYSTEMS AND METHODS FOR PROCESSING ELECTRONIC IMAGES FOR BIOMARKER LOCALIZATION

RELATED APPLICATION(S)

This application claims priority to U.S. Provisional Application No. 62/966,723 filed Jan. 28, 2020, the entire disclosure of which is hereby incorporated herein by reference in its entirety.

FIELD OF THE DISCLOSURE

Various embodiments of the present disclosure pertain generally to localization of biomarkers and/or inferring spatial relationships in a digital pathology slide. More specifically, particular embodiments of the present disclosure relate to systems and methods for tumor and invasive margin detection, localized biomarker prediction, and/or biomarker and spatial relationship comparison. The present disclosure further provides systems and methods for using artificial intelligence (AI) to spatially infer various genomic features, molecular tests, and other analyses.

BACKGROUND

Comprehensive genetic and molecular testing of cancer tissue may allow for precision treatment of solid tumors via targeted therapies. Even though the cost of genome sequencing has substantially decreased over the years, these tests are still costly, slow, and require substantial amount of tissue that is quite limited in clinical studies. Hematoxylin and Eosin (H&E) staining is affordable and provides a comprehensive visual description of the tumor and its microenvironment.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for biomarker localization within tumor microenvironment and in the invasive margin of the tumor using artificial intelligence (AI).

A computer-implemented method for analyzing an image corresponding to a specimen, includes: receiving one or more digital images of a pathology specimen from a patient, the pathology specimen comprising tumor tissue, the one or more digital images being associated with data about a plurality of biomarkers in the tumor tissue and data about a surrounding invasive margin around the tumor tissue; identifying the tumor tissue and the surrounding invasive margin region to be analyzed for each of the one or more digital images; generating, using a machine learning model on the one or more digital images, at least one inference of a presence of the plurality of biomarkers in the tumor tissue and the surrounding invasive margin region; determining a spatial relationship of each of the plurality of biomarkers identified in the tumor tissue and the surrounding invasive margin region to themselves and other cell types; and determining, based on the spatial relationship of each of the plurality of biomarkers to themselves or other cell types, a prediction for a treatment outcome and/or at least one treatment recommendation for the patient.

In accordance with another embodiment, a system for analyzing an image corresponding to a specimen, includes: receiving one or more digital images of a pathology specimen from a patient, the pathology specimen comprising tumor tissue, the one or more digital images being associated with data about a plurality of biomarkers in the tumor tissue and data about a surrounding invasive margin around the tumor tissue; identifying the tumor tissue and the surrounding invasive margin region to be analyzed for each of the one or more digital images; generating, using a machine learning model on the one or more digital images, at least one inference of a presence of the plurality of biomarkers in the tumor tissue and the surrounding invasive margin region; determining a spatial relationship of each of the plurality of biomarkers identified in the tumor tissue and the surrounding invasive margin region to themselves and other cell types; and determining, based on the spatial relationship of each of the plurality of biomarkers to themselves and other cell types, a prediction for a treatment outcome and/or at least one treatment recommendation for the patient.

In accordance with another embodiment, at least one non-transitory computer-readable medium storing instructions performing a method for analyzing an image corresponding to a specimen, the at least one non-transitory computer readable medium storing instructions which, when executed by one or more processors, cause the one or more processors to perform operations including: receiving one or more digital images of a pathology specimen from a patient, the pathology specimen comprising tumor tissue, the one or more digital images being associated with data about a plurality of biomarkers in the tumor tissue and data about a surrounding invasive margin around the tumor tissue; identifying the tumor tissue and the surrounding invasive margin region to be analyzed for each of the one or more digital images; generating, using a machine learning model on the one or more digital images, at least one inference of a presence of the plurality of biomarkers in the tumor tissue and the surrounding invasive margin region; determining a spatial relationship of each of the plurality of biomarkers identified in the tumor tissue and the surrounding invasive margin region to themselves and other cell types; and determining, based on the spatial relationship of each of the plurality of biomarkers to themselves and other cell types, a prediction for a treatment outcome and/or at least one treatment recommendation for the patient.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
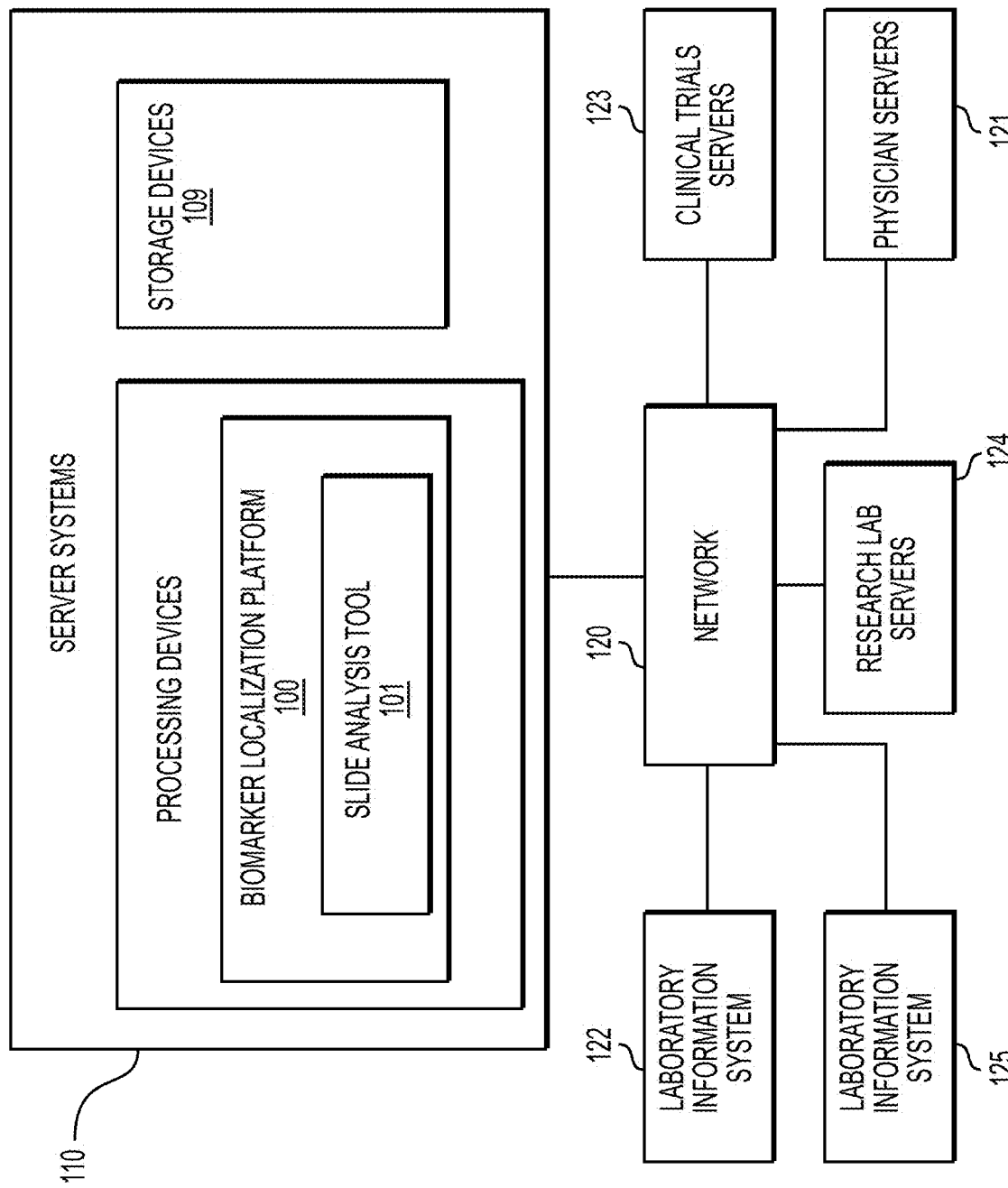
FIG. 1A illustrates an exemplary block diagram of a system and network for localizing biomarkers and inferring spatial relationships, using machine learning, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) that may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a consolidated workflow for improving diagnosis of cancer and other diseases. The workflow may integrate, for example, slide evaluation, tasks, image analysis and cancer detection artificial intelligence (AI), annotations, consultations, and recommendations in one workstation. In particular, the present disclosure describes various exemplary user interfaces available in the workflow, as well as AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline. This automation may have, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, nissl and methylene blue, and Hematoxylin and Eosin (H&E). For medical diagnosis, H&E is a widely used dye-based method, with hematoxylin staining cell nuclei blue, eosin staining cytoplasm and extracellular matrix pink, and other tissue regions taking on variations of these colors. In many cases, however, H&E-stained histologic preparations do not provide sufficient information for a pathologist to visually identify biomarkers that can aid diagnosis or guide treatment. In this situation, techniques such as immunohistochemistry (IHC), immunofluorescence, in situ hybridization (ISH), or fluorescence in situ hybridization (FISH), may be used. IHC and immunofluorescence involve, for example, using antibodies that bind to specific antigens in tissues enabling the visual detection of cells expressing specific proteins of interest, which can reveal biomarkers that are not reliably identifiable to trained pathologists based on the analysis of H&E stained slides. ISH and FISH may be employed to assess the number of copies of genes or the abundance of specific RNA molecules, depending on the type of probes employed (e.g. DNA probes for gene copy number and RNA probes for the assessment of RNA expression). If these methods also fail to provide sufficient information to detect some biomarkers, genetic testing of the tissue may be used to confirm if a biomarker is present (e.g., overexpression of a specific protein or gene product in a tumor, amplification of a given gene in a cancer).

A digitized image may be prepared to show a stained microscope slide, which may allow a pathologist to manually view the image on a slide and estimate a number of stained abnormal cells in the image. However, this process may be time consuming and may lead to errors in identifying abnormalities because some abnormalities are difficult to detect. Computational processes and devices may be used to assist pathologists in detecting abnormalities that may otherwise be difficult to detect. For example, AI may be used to predict biomarkers (such as the over-expression of a protein and/or gene product, amplification, or mutations of specific genes) from salient regions within digital images of tissues stained using H&E and other dye-based methods. The images of the tissues could be whole slide images (WSI), images of tissue cores within microarrays or selected areas of interest within a tissue section. Using staining methods like H&E, these biomarkers may be difficult for humans to visually detect or quantify without the aid of additional testing. Using AI to infer these biomarkers from digital images of tissues has the potential to improve patient care, while also being faster and less expensive.

The detected biomarkers or the image alone could then be used to recommend specific cancer drugs or drug combination therapies to be used to treat a patient. The AI may identify which drugs or drug combinations are unlikely to be successful by correlating the detected biomarkers with a database of treatment options. This can be used to facilitate the automatic recommendation of immunotherapy or targeted treatments for a patient's specific cancer. Further, this could be used for enabling personalized cancer treatment for specific subsets of patients and/or rarer cancer types.

As described above, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The digital pathology images described above may be stored with tags and/or labels pertaining to the properties of the specimen or image of the digital pathology image, and such tags/labels may be incorrect or incomplete. Accordingly, the present disclosure is directed to systems and methods for identifying or verifying correct properties (e.g., pertaining to a specimen type) of a digital pathology image. In particular, the disclosed systems and methods may automatically predict the specimen or image properties of a digital pathology image, without relying on the stored tags/labels. Further, the present disclosure is directed to systems and methods for quickly and correctly identifying and/or verifying a specimen type of a digital pathology image, or any information related to a digital pathology image, without necessarily accessing an LIS or analogous information database. One embodiment of the present disclosure may include a system trained to identify various properties of a digital pathology image, based on datasets of prior digital pathology images. The trained system may provide a classification for a specimen shown in a digital pathology image. The classification may help to provide treatment or diagnosis prediction(s) for a patient associated with the specimen.

This disclosure includes one or more embodiments of a specimen classification tool. The input to the tool may include a digital pathology image and any relevant additional inputs. Outputs of the tool may include global and/or local information about the specimen. A specimen may include a biopsy or surgical resection specimen.

Exemplary global outputs of the disclosed tool(s) may contain information about an entire image, e.g., the specimen type, the overall quality of the cut of the specimen, the overall quality of the glass pathology slide itself, and/or tissue morphology characteristics. Exemplary local outputs may indicate information in specific regions of an image, e.g., a particular image region may be classified as having blur or a crack in the slide. The present disclosure includes embodiments for both developing and using the disclosed specimen classification tool(s), as described in further detail below.

The present disclosure uses artificial intelligence (AI) to infer spatially localized genetic, molecular (e.g., the over-expression of a protein and/or a gene product, amplification, mutations of specific genes), flow cytometry and immune markers (tumor infiltrating lymphocytes, macrophages, etc.) from digital images of stained pathology specimens. The images of the tissues could be whole slide images (WSI), images of tissue cores within microarrays or selected areas of interest within a tissue section. Localization of biomarkers from digital images of tissues may have the potential to develop faster, cheaper as well as newer/more novel diagnostic tests. Furthermore, localization of biomarkers from both tumor tissue and surrounding tumor tissue (invasive margin) may have prognostic value. For example, the amount of tumor infiltrating lymphocytes (TILs) within and in the invasive margin of a tumor has prognostic value, and may be used to determine which patients will be likely to respond to immunotherapies (e.g., Immunoscore). Understanding spatial relationships of one or more biomarkers within a tumor and the invasive margin of the tumor to themselves and other cell types may enable better treatments and more accurate patient stratification strategies.

The present embodiments may use AI to spatially infer various genomic, molecular tests from stained histologic sections, thus allowing multiplex analysis. After localizing the biomarkers, spatial relationships of these biomarkers to themselves and to other cell types may be investigated. The spatial relationships may be predictive of cancer outcomes and therapies. Furthermore, a comprehensive analysis that involves localizing tumor markers within a surrounding area (invasive margin) of the tumor may facilitate better understanding of tumor biology and enable development of new and novel biomarkers and treatments.

The present embodiments may provide tumor region and invasive margin detection that may be used to determine the spatial location of biomarkers of diagnostic relevance. A genetic or molecular test obtained from a cancer tissue may utilize the tumor region and invasive margin detection embodiments to confine the analysis to a relevant region.

FIG. 1A illustrates a block diagram of a system and network for localizing biomarkers and inferring spatial relationships, using machine learning, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a biomarker localization platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a LIS 125. However, the correct tissue classification information is not always paired with the image content. Additionally, even if an LIS is used to access the specimen type for a digital pathology image, this label may be incorrect due to the fact that many components of an LIS may be manually inputted, leaving a large margin for error. According to an exemplary embodiment of the present disclosure, a specimen type may be identified without needing to access the LIS 125, or may be identified to possibly correct LIS 125. For example, a third party may be given anonymized access to the image content without the corresponding specimen type label stored in the LIS. Additionally, access to LIS content may be limited due to its sensitive content.

Figure 1B:
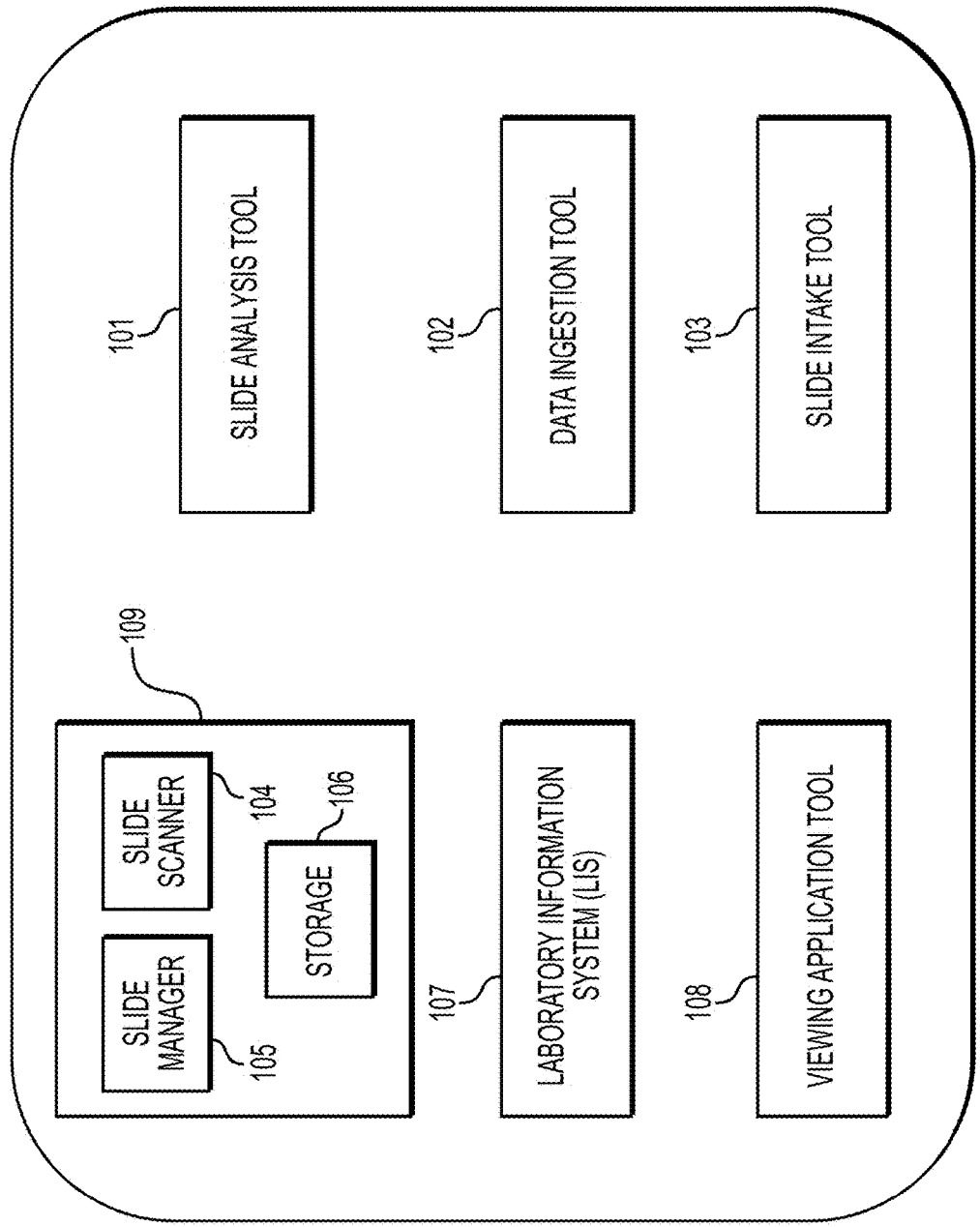
FIG. 1B illustrates an exemplary block diagram of a biomarker localization platform, according to techniques presented herein.

FIG. 1B illustrates an exemplary block diagram of a biomarker localization platform 100 for determining specimen property or image property information pertaining to digital pathology image(s), using machine learning.

Specifically, FIG. 1B depicts components of the biomarker localization platform 100, according to one embodiment. For example, the biomarker localization platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for determining specimen property or image property information pertaining to digital pathology image(s), and using machine learning to classify a specimen, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools, and modules may be located on a device that may be connected to an electronic network 120, such as the Internet or a cloud service provider, through one or more computers, servers, and/or handheld mobile devices.

Figure 1C:
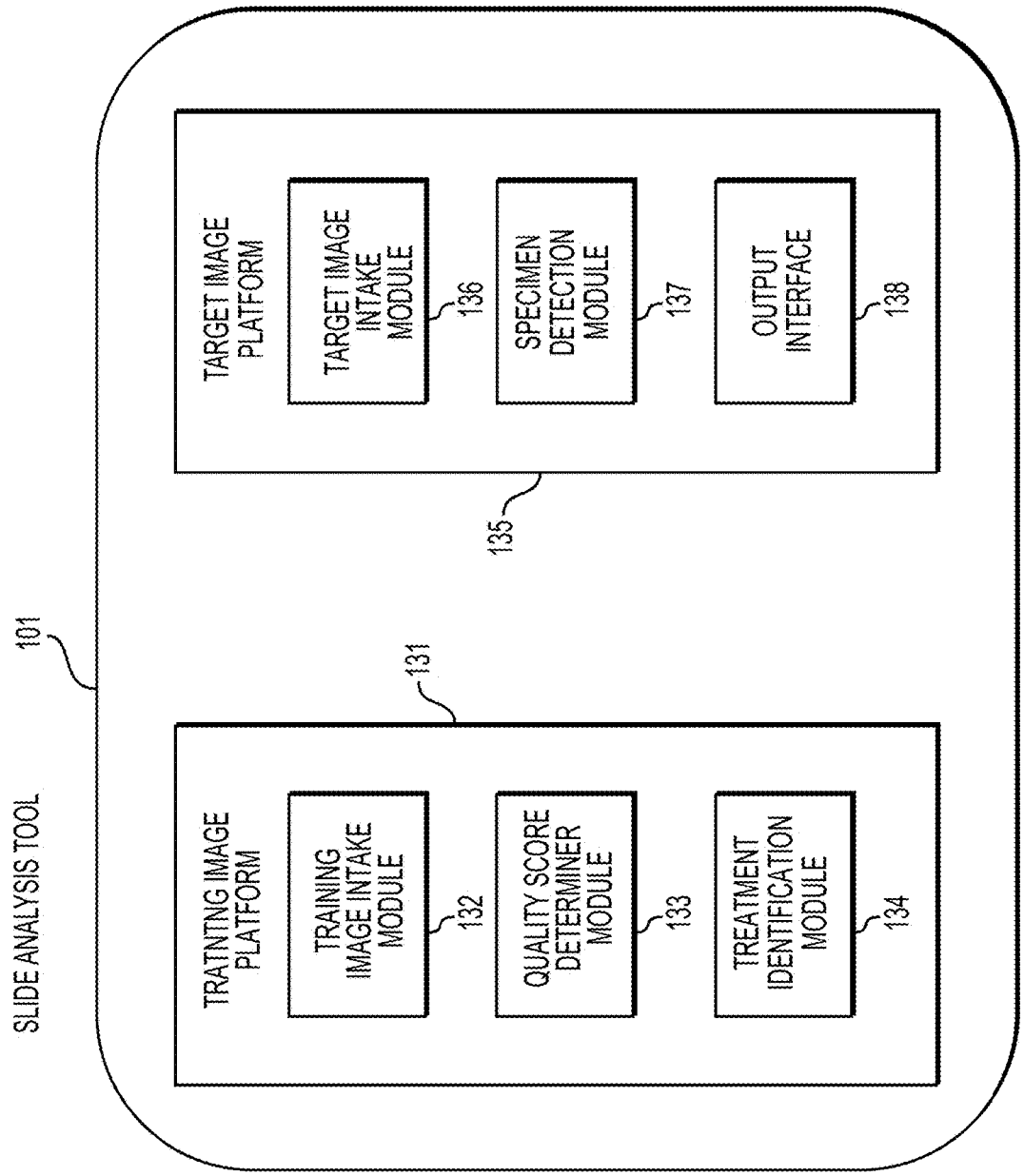
FIG. 1C illustrates an exemplary block diagram of a slide analysis tool, according to techniques presented herein.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a quality score determiner module 133, and/or a treatment identification module 134.

The training image platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training images corresponding to either or both of images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. The quality score determiner module 133 may identify quality control (QC) issues (e.g., imperfections) for the training images at a global or local level that may greatly affect the usability of a digital pathology image. For example, the quality score determiner module may use information about an entire image, e.g., the specimen type, the overall quality of the cut of the specimen, the overall quality of the glass pathology slide itself, or tissue morphology characteristics, and determine an overall quality score for the image. The treatment identification module 134 may analyze images of tissues and determine which digital pathology images have treatment effects (e.g., post-treatment) and which images do not have treatment effects (e.g., pre-treatment). It is useful to identify whether a digital pathology image has treatment effects because prior treatment effects in tissue may affect the morphology of the tissue itself. Most LIS do not explicitly keep track of this characteristic, and thus classifying specimen types with prior treatment effects can be desired.

According to one embodiment, the target image platform 135 may include a target image intake module 136, a specimen detection module 137, and an output interface 138. The target image platform 135 may receive a target image and apply the machine learning model to the received target image to determine a characteristic of a target specimen. For example, the target image may be received from any one or any combination of the server systems 110, physician servers 121, hospital servers 122, clinical trial servers 123, research lab servers 124, and/or laboratory information systems 125. The target image intake module 136 may receive a target image corresponding to a target specimen. The specimen detection module 137 may apply the machine learning model to the target image to determine a characteristic of the target specimen. For example, the specimen detection module 137 may detect a specimen type of the target specimen. The specimen detection module 137 may also apply the machine learning model to the target image to determine a quality score for the target image. Further, the specimen detection module 137 may apply the machine learning model to the target specimen to determine whether the target specimen is pre-treatment or post-treatment.

The output interface 138 may be used to output information about the target image and the target specimen. (e.g., to a screen, monitor, storage device, web browser, etc.).

Figure 2A:
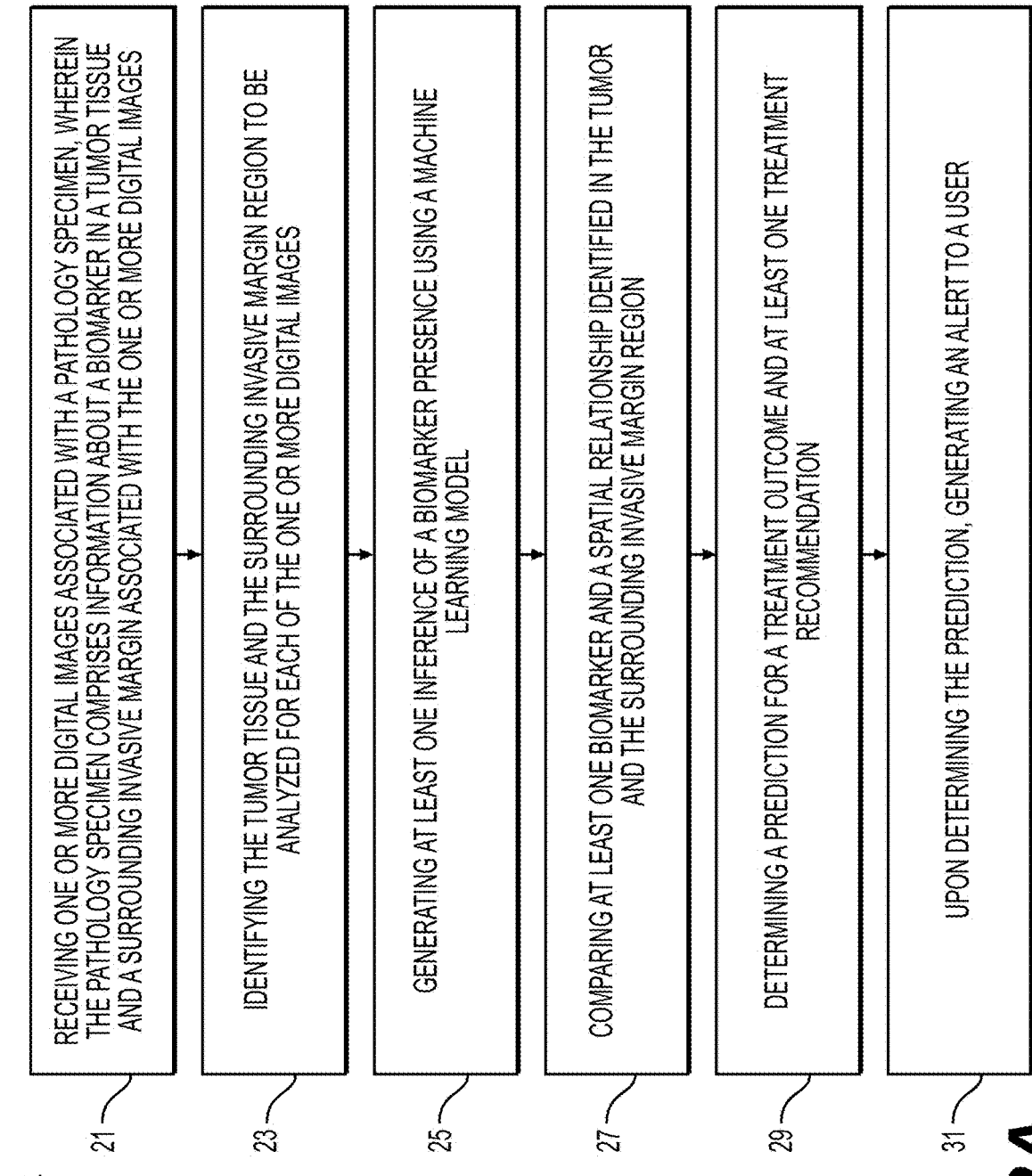
FIG. 2A is a flowchart illustrating an exemplary method for use of a biomarker localization within tumor microenvironment using AI, according to techniques presented herein.

FIG. 2A is a flowchart illustrating an exemplary method for use of a biomarker localization within tumor microenvironments using AI, according to an exemplary embodiment of the present disclosure. For example, an exemplary method 20 (e.g., steps 21-31) may be performed by slide analysis tool 101 automatically or in response to a request from a user.

According to one embodiment, the exemplary method 20 for localizing a biomarker and inferring relationships may include one or more of the following steps. In step 21, the method may include receiving one or more digital images associated with a pathology specimen, wherein the pathology specimen comprises information about a biomarker in a tumor tissue and a surrounding invasive margin associated with the one or more digital images. The pathology specimen may comprise a histology specimen, a cytology specimen, etc. The one or more digital images may be received into a digital storage device (e.g., hard drive, network drive, cloud storage, RAM, etc.). To train a machine learning model, each image may be paired with information about the biomarkers in the tumor and surrounding invasive margin tissues associated with each respective image. The information may be identified from genetic testing, flow cytometry, IHC, etc. analyzed by a pathologist, pathologist measurements, etc. A machine learning model may comprise a machine learning algorithm.

In step 23, the method may include identifying the tumor tissue and the surrounding invasive margin region to be analyzed for each of the one or more digital images. This may be done manually by a human or automatically using AI.

In step 25, the method may include generating at least one inference of a biomarker presence using a machine learning model. The method may also include using computer vision. The biomarker may be present in the tumor tissue and the surrounding invasive margin image region(s). A prediction from the at least one inference may be output to an electronic storage device. An embodiment may involve generating an alert to notify a user of the presence or absence of one or more of the biomarkers.

In step 27, the method may include comparing at least one biomarker and a spatial relationship (e.g., a relative position or proximity of clusters within biomarkers and/or to other cell types, etc.) identified in the tumor and the surrounding invasive margin region. Various studies have demonstrated metrics based on spatial relationship of various biomarkers and/or to other cell types within the tumor and the surrounding invasive margin can provide insights on cancer recurrence, metastasis and treatment response.

In step 29, the method may include determining a prediction for a treatment outcome and at least one treatment recommendation.

In step 31, the method may include, upon determining the prediction, generating an alert to a user. The alert may be a visual popup, a noise, or any other suitable alert method.

Figure 2B:
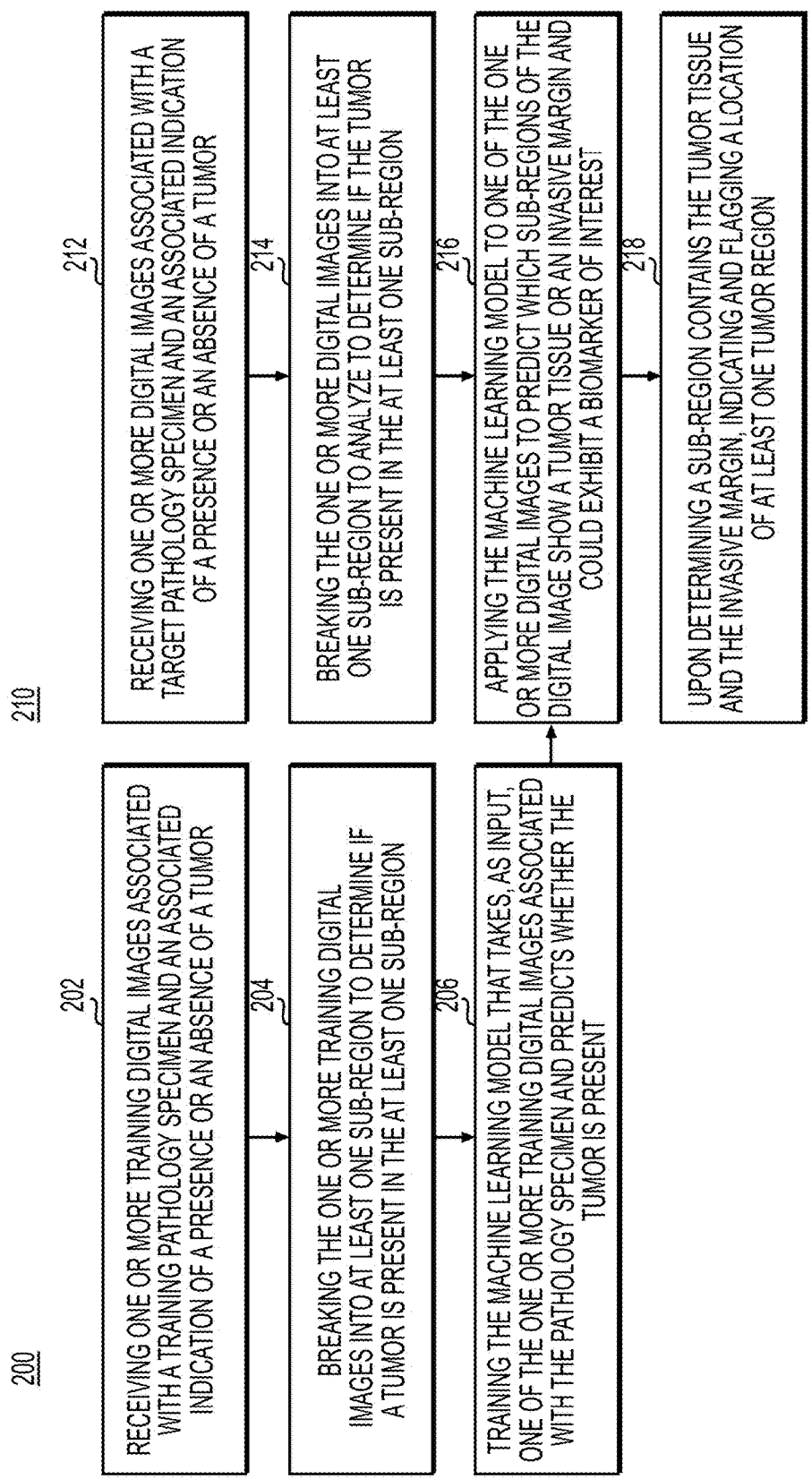
FIG. 2B is a flowchart illustrating an exemplary method for training and using a tumor and invasive margin detection module using AI, according to techniques presented herein.

FIG. 2B is a flowchart illustrating an exemplary method for training and using a tumor and invasive margin detection module using machine learning, according to an exemplary embodiment of the present disclosure. The prevalence of biomarkers within a tumor is of interest and tumor regions may take up only a small fraction of the entire image. With new advances in immunotherapies, it has been demonstrated that cellular activity in the invasive region (e.g., neighboring non-tumor regions of the tumor) may also provide valuable information on outcome. Hence, it may be crucial to identify biomarkers both in a tumor and in its invasive margin (neighboring non tumor regions). These regions of interest may be specified by a human expert using an image segmentation, a bounding box, or a polygon. Alternatively, a complete end-to-end solution may include using AI to identify the appropriate locations of such regions of interest. Automatic tumor and invasive margin identification may enable a downstream AI system to learn how to detect biomarkers from less annotated data and to make more accurate predictions.

There may be two general approaches to creating a tumor and invasive margin detector: strongly supervised methods that may identify precisely where the biomarkers could be found and weakly supervised methods that may not provide a precise location. During training, the strongly supervised system may receive, as input, an image. The strongly supervised system may further receive, for the image, a location of a tumor and invasive margin region(s) that expresses the biomarker. These locations may be specified with pixel-level labeling, tile-level labeling, bounding box-based labeling, polygon-based labeling, or using a corresponding image where the tumor and the invasive margins have been identified (e.g., using Immunohistochemistry (IHC)). The weakly supervised system may receive, as input, an image and the presence/absence of a tumor and invasive regions in the image. The exact location of the tumor and the invasive margin locations may not be specified in the input for the weakly supervised system. The weakly supervised system can then be run in a localized way over regions to determine tumor, invasive margin, and non-tumor regions. For neural network and end-to-end learning approaches, evidence visualization methods (e.g., GradCAM) can be utilized to localize tumor, invasive margin and non-tumor tissue regions.

According to one embodiment, the exemplary methods 200 and 210 for training and using the tumor and invasive margin detection module may include one or more of the following steps. In step 202, the method may include receiving one or more training digital images associated with a training pathology specimen and an associated indication of a presence or an absence of a tumor region. The training pathology specimen may comprise a histology specimen, a cytology specimen, etc. The training digital images may be received into a digital storage device (e.g., hard drive, network drive, cloud storage, RAM, etc.).

In step 204, the method may include breaking the one or more training digital images into at least one sub-region to determine if the tumor is present in the at least one sub-region. Sub-regions may be specified in a variety of methods, including creating tiles of the image, segmentation-based on edges or contrast, segmentations via color differences, supervised determination by the machine learning model, EdgeBoxes, etc.

In step 206, the method may include training the machine learning model that takes, as input, one of the one or more training digital images associated with the pathology specimen and predicts whether the tumor is present. A number of methods may be used to learn which image regions show tumor tissue and which regions show invasive margin(s), including but not limited to:

Weak supervision: training a machine learning model (e.g., multi-layer perceptron (MLP), convolutional neural network (CNN), graph neural network, support vector machine (SVM), random forest, etc.) using multiple instance learning (MIL) using weak labeling of the digital image or a collection of images. The label may correspond to the presence or absence of a tumor region.

Bounding box or polygon-based supervision: training a machine learning model (e.g., R-CNN, Faster R-CNN, Selective Search) using bounding boxes or polygons that specify the sub-regions of the digital image that show tumor tissue or invasive margins.

Pixel-level labeling (e.g., a semantic or instance segmentation): training a machine learning model (e.g., Mask R-CNN, U-net, Fully Convolutional Neural Network) using a pixel-level labeling, where individual pixels may be identified as showing tumor tissue or invasive margins.

Using a corresponding, but different digital image that identifies tumor tissue regions: a digital image of tissue that highlights the tumor region and invasive margin (e.g., tumor/invasive margin identified using IHC) may be registered with the input digital image. For example, a digital image of an H&E image could be registered or aligned with an IHC image identifying tumor and invasive margin tissue, where the IHC may be used to determine the tumor pixels by looking at image color characteristics.

In step 212, the method may include receiving one or more digital images associated with a target pathology specimen and an associated indication of a presence or an absence of a tumor. The target pathology specimen may comprise a histology specimen, a cytology specimen, etc. The one or more digital images may be received into a digital storage device (e.g., hard drive, network drive, cloud storage, RAM, etc.).

In step 214, the method may include breaking the one or more digital images into at least one sub-region to determine if the tumor is present in the at least one sub-region. Regions may be specified in a variety of methods, including creating tiles of the image, edge or contrast, segmentations via color differences, supervised determination by the machine learning model, EdgeBoxes, etc.

In step 216, the method may include applying the machine learning model to one of the one or more digital images to predict which regions of the digital image show a tumor tissue or an invasive margin and could exhibit a biomarker of interest.

In step 218, the method may include, upon determining a sub-region contains the tumor tissue or the invasive margin, indicating and flagging a location of at least one tumor region. Detecting the tumor tissue and invasive margin regions may be done using a variety of methods, including but not restricted to:

a) Running the trained machine learning model on image sub-regions to generate the prediction for each image sub-region.

b) Using machine learning visualization tools to create a detailed heatmap, e.g., by using class activation maps, GradCAM, etc., and then extracting the relevant regions.

Figure 2C:
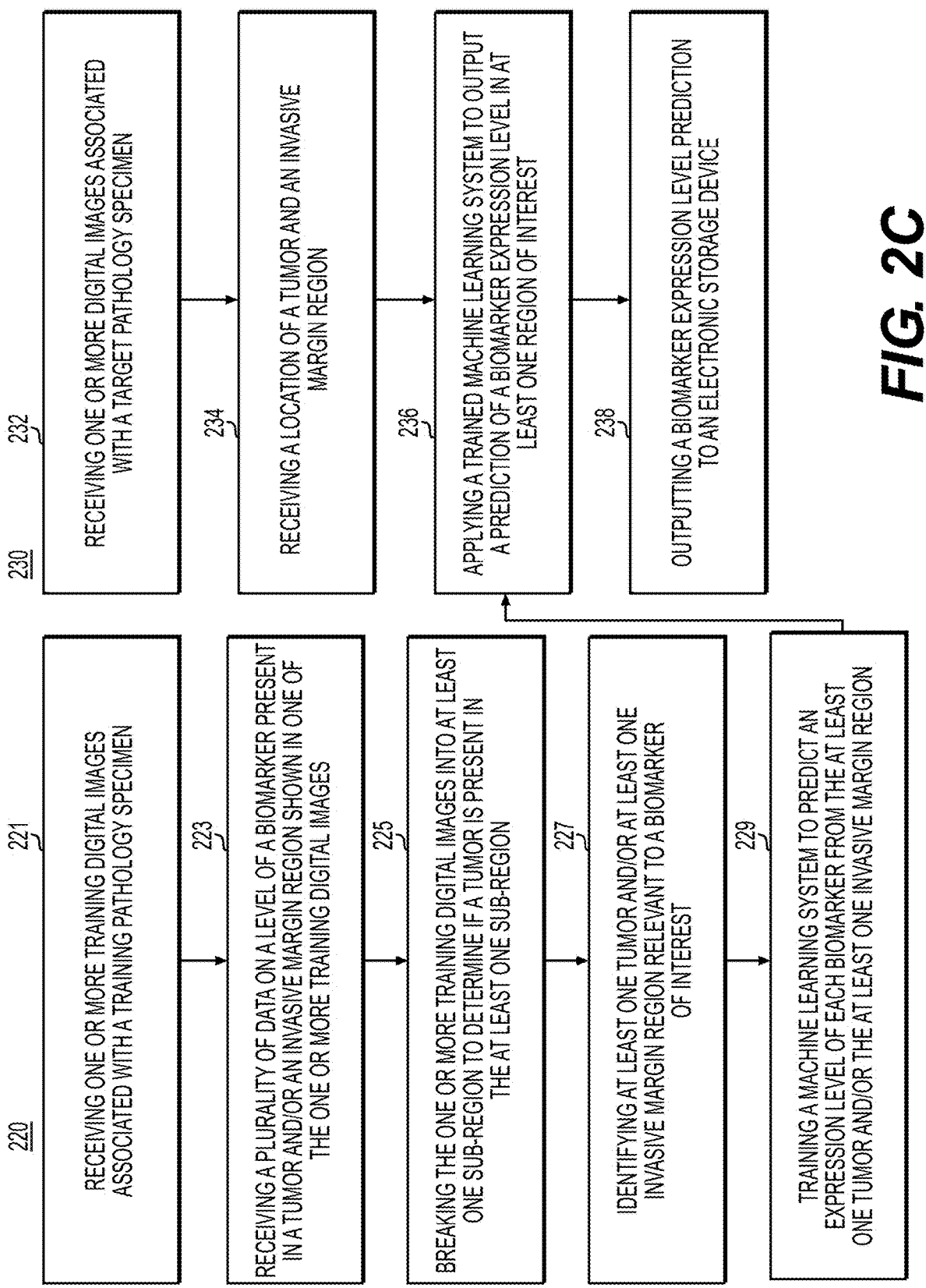
FIG. 2C is a flowchart illustrating an exemplary method for training and using a localized biomarker prediction module, according to techniques presented herein.

FIG. 2C is a flowchart illustrating an exemplary method of training 220 and a method of using a localized biomarker prediction module 230, using machine learning, according to an exemplary embodiment of the present disclosure. Biomarkers may include genomic results, IHC or outcome results. Identification of localized biomarkers from H&E slides may enable more precision therapy, while reducing cost, turnaround time, and interobserver interpreter variability. AI-based inference of localized biomarkers may provide information on tumor biology and microenvironment (e.g., the interaction of various cell types with a tumor), which may allow more accurate patient stratification strategies. An AI based inference of localized H&E based genotyping/molecular/immune marker testing may allow rapid screening of patients that may require a more comprehensive molecular test, or rapid screening for selecting patients that may benefit most in targeted therapies. The below embodiments may be used to predict any biomarkers that are used in clinical trials such as flow cytometry, blood assays, etc.

According to one embodiment, the exemplary method of training and using the localized biomarker prediction module may include one or more of the following steps. In step 221, the method may include receiving one or more training digital images associated with a training pathology specimen. The training pathology specimen may comprise a histology specimen, a cytology specimen, etc. The training digital images may be received into a digital storage device (e.g., hard drive, network drive, cloud storage, RAM, etc.).

In step 223, the method may include receiving a plurality of data on a level of a biomarker present in a tumor and/or an invasive margin region shown in one or the one or more training digital images. The biomarker presence may be indicated with a binary or an ordinal value.

In step 225, the method may include breaking the one or more training digital images into at least one sub-region to determine if a tumor is present in the at least one sub-region. Breaking the one or more training digital images into sub-regions may be based on sub-region properties. Sub-regions may be specified in a variety of methods, including creating tiles of the image, segmentations, based on edges or contrast, segmentations via color differences, supervised determination by the machine learning model, etc.

In step 227, the method may include identifying at least one tumor and/or at least one invasive margin region relevant to a biomarker of interest. This may be done using an AI-based system or using manual annotations from an expert.

In step 229, the method may include training a machine learning system to predict an expression level of each biomarker from the at least one tumor and/or the at least one invasive margin region. Expression levels may be represented as binary numbers, ordinal numbers, real numbers, etc. This algorithm may be implemented in multiple ways, including but not limited to:
a) CNN
b) CNN with MIL
c) Recurrent Neural Network
d) Long-short term memory RNN (LSTM)
e) Gated recurrent unit RNN (GRU)
f) Graph convolutional network
g) Support vector machine
h) Random forest In step 232, the method may include receiving one or more digital images associated with a target pathology specimen. The target pathology specimen may comprise a histology specimen, a cytology specimen, etc. The one or more digital images may be received into a digital storage device (e.g., hard drive, network drive, cloud storage, RAM, etc.).

In step 234, the method may include receiving a location of a tumor and an invasive margin region. The location may be automatically or manually specified by an expert.

In step 236, the method may include applying a trained machine learning system to output a prediction of a biomarker expression level in at least one region of interest.

In step 238, the method may include outputting a biomarker expression level prediction to an electronic storage device. The method may additionally include generating a visual indicator to alert the user (e.g., a pathologist, a histology technician, etc.) to the presence of the biomarker.

Figure 2D:
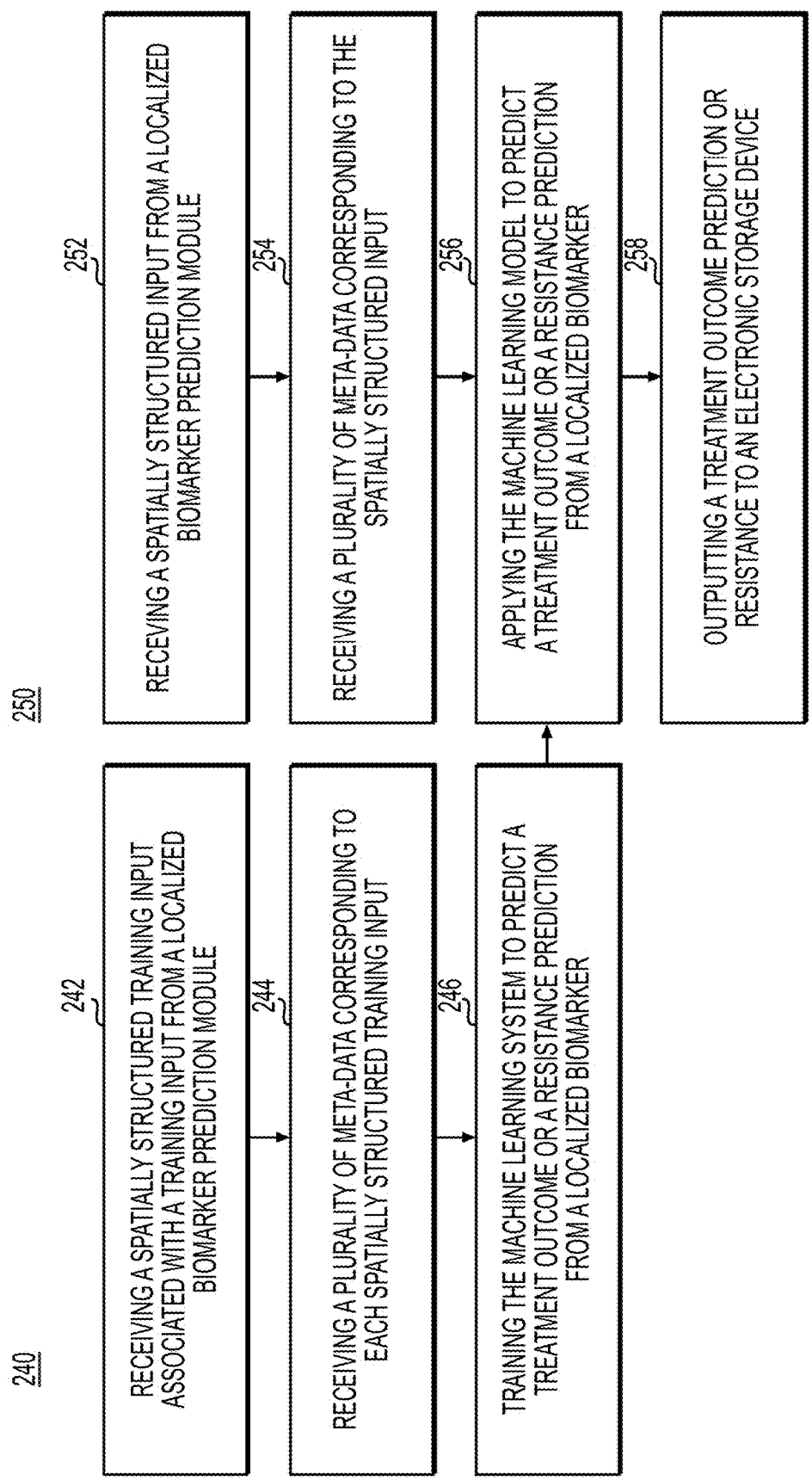
FIG. 2D is a flowchart illustrating an exemplary method for training and using a biomarker comparison module, according to techniques presented herein.

FIG. 2D is a flowchart illustrating an exemplary method of training and using the biomarker comparison module, using machine learning, according to an exemplary embodiment of the present disclosure. The biomarker comparison module may take, as input, spatially organized biomarker signatures or vector embeddings of the spatially organized biomarkers and infer information using AI, e.g., treatment outcome, treatment resistance, etc. Exemplary methods 240 and 250 may be performed by slide analysis tool 101 automatically or in response to a request from a user.

According to one embodiment, the exemplary methods 240 and 250 for training and using the biomarker comparison module may include one or more of the following steps. In step 242, the method may include receiving a spatially structured training input associated with a training input from a localized biomarker prediction module. The spatially structured input from the localized biomarker prediction module may comprise information about whether the location lies in a tumor, an invasive margin, outside the tumor, etc.

In step 244, the method may include receiving a plurality of metadata corresponding to each spatially structured training input. The metadata may comprise demographic information, patient history, etc.

In step 246, the method may include training the machine learning system to predict a treatment outcome or a resistance prediction from a localized biomarker. Training the machine learning system may comprise an algorithm implemented in multiple ways, including but not limited to:
a. CNN
b. CNN trained with MIL
c. Recurrent neural network
d. Long-short term memory RNN (LSTM)
e. Gated recurrent unity RNN (GRU)
f. Graph convolutional network
g. Support vector machine
h. Random forest In step 252, the method may include receiving a spatially structured input from a localized biomarker prediction module. The input from the localized biomarker prediction module may include high-level variables or vector embeddings. Each spatial structure location may contain information about whether the location lies in the tumor, invasive margin, outside the tumor, etc.

In step 254, the method may include receiving a plurality of meta-data corresponding to the spatially structured input (e.g., demographic information, patient history, etc.).

In step 256, the method may include applying the machine learning model to predict the treatment outcome or a resistance prediction from a localized biomarker.

In step 258, the method may include outputting a treatment outcome or resistance prediction to an electronic storage device. The method may also include generating a visual indicator to alert a user (e.g., a pathologist, histology technician, etc.) to the outcome information.

Figure 3:
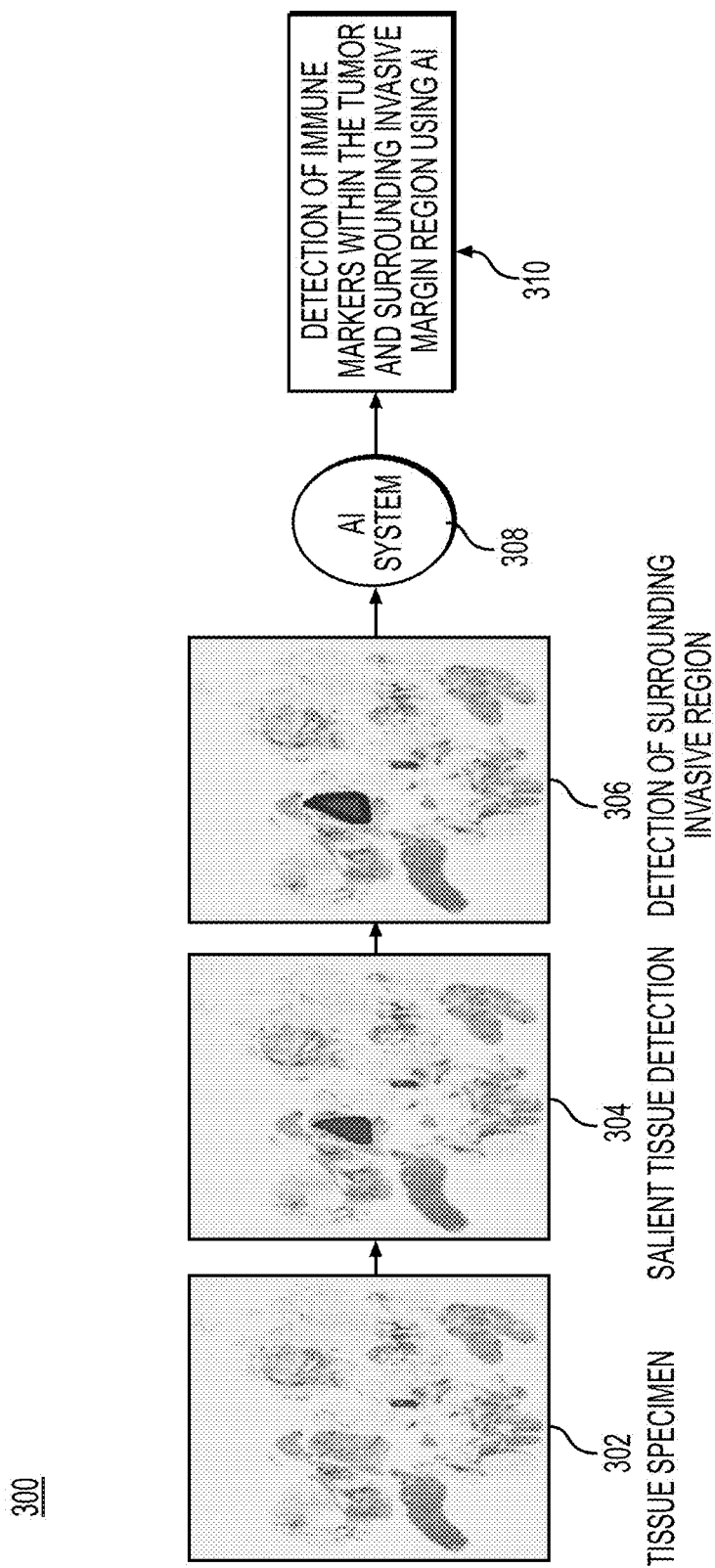
FIG. 3 is an exemplary system trained to detect immune markers within a tumor and surrounding invasive margin, according to techniques presented herein.

FIG. 3 is an exemplary system trained to detect immune markers within a tumor and surrounding invasive margin, according to an exemplary embodiment of the present disclosure. The exemplary embodiment 300 (e.g., steps 302-310) may be performed by slide analysis tool 101 automatically or in response to a request from a user.

Exemplary embodiment 300 presents the steps for detecting immune markers within the tumor and surrounding invasive margin of the tumor which has prognostic implications for cancer recurrence, metastasis and treatment response. Embodiment 300 may include one or more of the following steps. In step 302, the method may include an algorithm is fed a digital whole slide image of a breast tissue, where some of the tissue is cancerous. In step 304, the method may include the salient tissue is detected by the algorithm. In step 306, the method may include a tumor tissue detector and invasive margin detector that may filter the image to focus on specific tissue regions that have cancer and neighboring non cancer tissue regions. The detection of invasive or neighboring non cancer tissue regions can be performed via various morphological or clustering approaches etc. In a step 308, the method may include an AI that may infer an expression level of each immune marker within the tumor and surrounding non-tumor region, using the tumor regions. In a step 310, the method may include detecting immune markers within the tumor and may further include detecting immune markers within the surrounding invasive margin region. Step 310 may be performed partly or entirely using machine learning.

Figure 4:
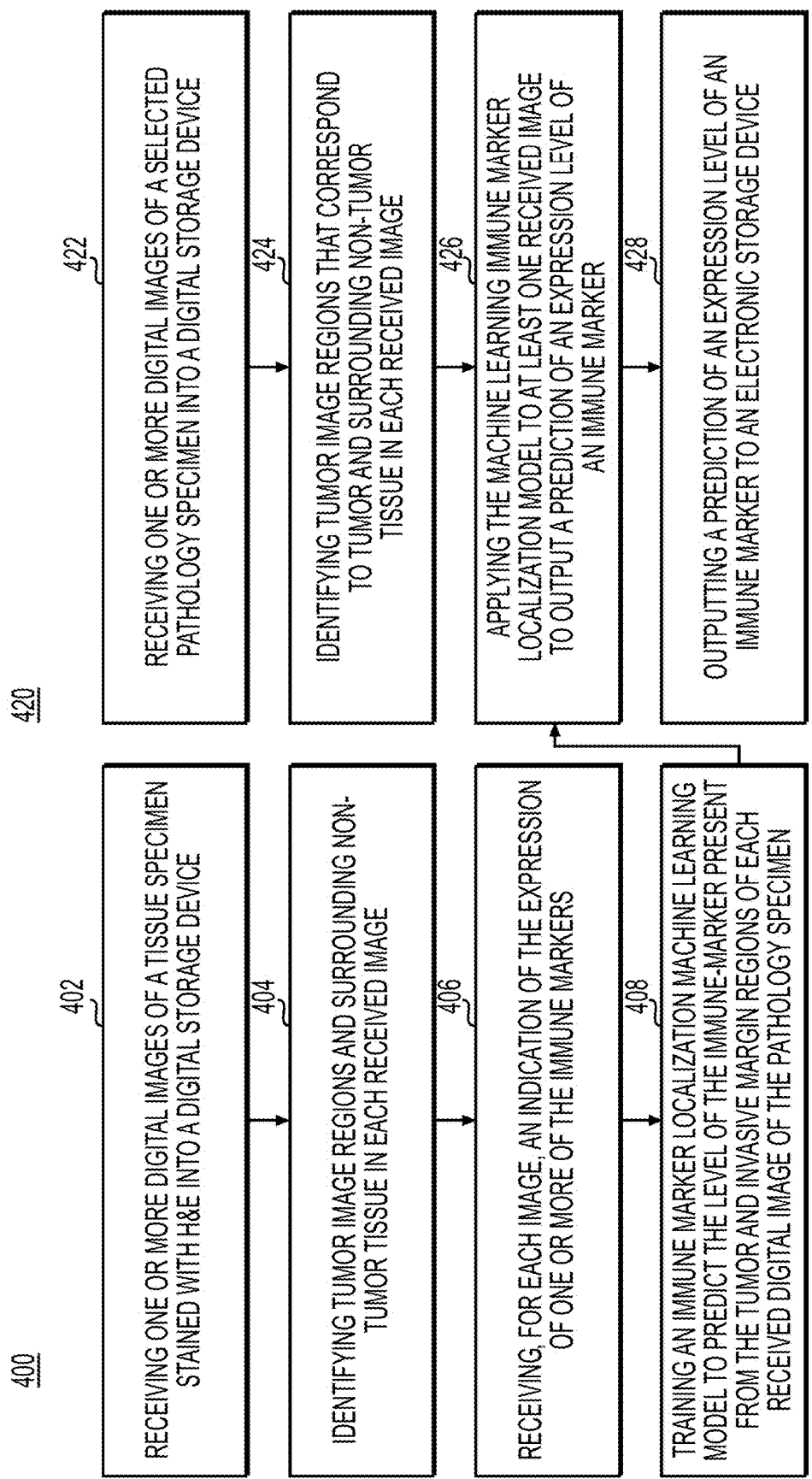
FIG. 4 is a flowchart illustrating an exemplary method for training and using a machine learning model to characterize immune markers in H&E, according to techniques presented herein.

FIG. 4 is a flowchart illustrating an exemplary method for training and using an immune marker localization model, according to an exemplary embodiment of the present disclosure. Identification of immune markers (e.g., tumor infiltrating lymphocytes (CD3 T-cells, CD8 T-cells, etc.), macrophages (CD68, CD163, etc.) may better characterize a patient's immune system and help to assess which patients are good candidates for immunotherapies. High levels of tumor infiltrating lymphocytes within and in an invasive margin of a tumor may be a good prognostic marker for cancer (e.g., Immunoscore). IHC may be used by pathologists to identify the expression and localization of these critical markers in tumor and invasive margin of the tumor tissue. In recent years, next generation sequencing technologies such as RNA-sequencing and flow cytometry have also been used for immunophenotyping, however the tissue architecture and any information about the spatial relationship between different cells may be lost in these technologies.

This embodiment comprises applying AI to predict immune markers from H&E stained digital images from various immunophenotyping methods. This embodiment may use the tumor/invasive margin region detector to identify tumor and non-surrounding non-tumor regions. The exemplary methods 400 and 420 (e.g., steps 402-408 and steps 422-428) may be performed by slide analysis tool 101 automatically or in response to a request from a user.

According to one embodiment, the exemplary method 400 for training the immune marker localization model may include one or more of the following steps. In step 402, the method may include receiving one or more digital images of a tissue specimen stained with H&E into a digital storage device (e.g., hard drive, network drive, cloud storage, RAM, etc.).

In step 404, the method may include identifying at least one tumor region and a surrounding tumor tissue in each received image, using either an AI-based method or manual specification.

In step 406, the method may include receiving, for each image, an indication of one or more of the immune markers (e.g., CD3, CD8, CD68, etc.). The level of immune marker expression may be identified using IHC, flow cytometry, RNA sequencing, etc. The level of expression may be on a numeric, ordinal, or binary scale. The indication may be assigned to the entire image or image subregions.

In step 408, the method may include training an immune marker localization machine learning model to predict the level of the immune marker present from the tumor and invasive margin regions of each of the received digital images of the pathology specimen.

In step 422, the method may include receiving one or more digital images of a selected pathology specimen into a digital storage device (e.g., hard drive, network drive, cloud storage, RAM, etc.).

In step 424, the method may include identifying tumor image regions that correspond to tumor and surrounding non-tumor tissue in each received image. This step may be performed by an AI-based method (e.g., the tumor/invasive margin region detection model) or manual specification.

In step 426, the method may include applying the machine learning marker localization model to at least one received image to output a prediction of an expression level or an immune marker.

In step 428, the method may include outputting a prediction of an expression level of an immune marker to an electronic storage device. The output may comprise generating a visual indication to alert the user (e.g., a pathologist, histology technician, etc.) of the expression levels of each immune marker. The output may additionally recommend treatments that may be effective for the tumor, given the predicted immune markers and their predicted expression levels.

Figure 5:
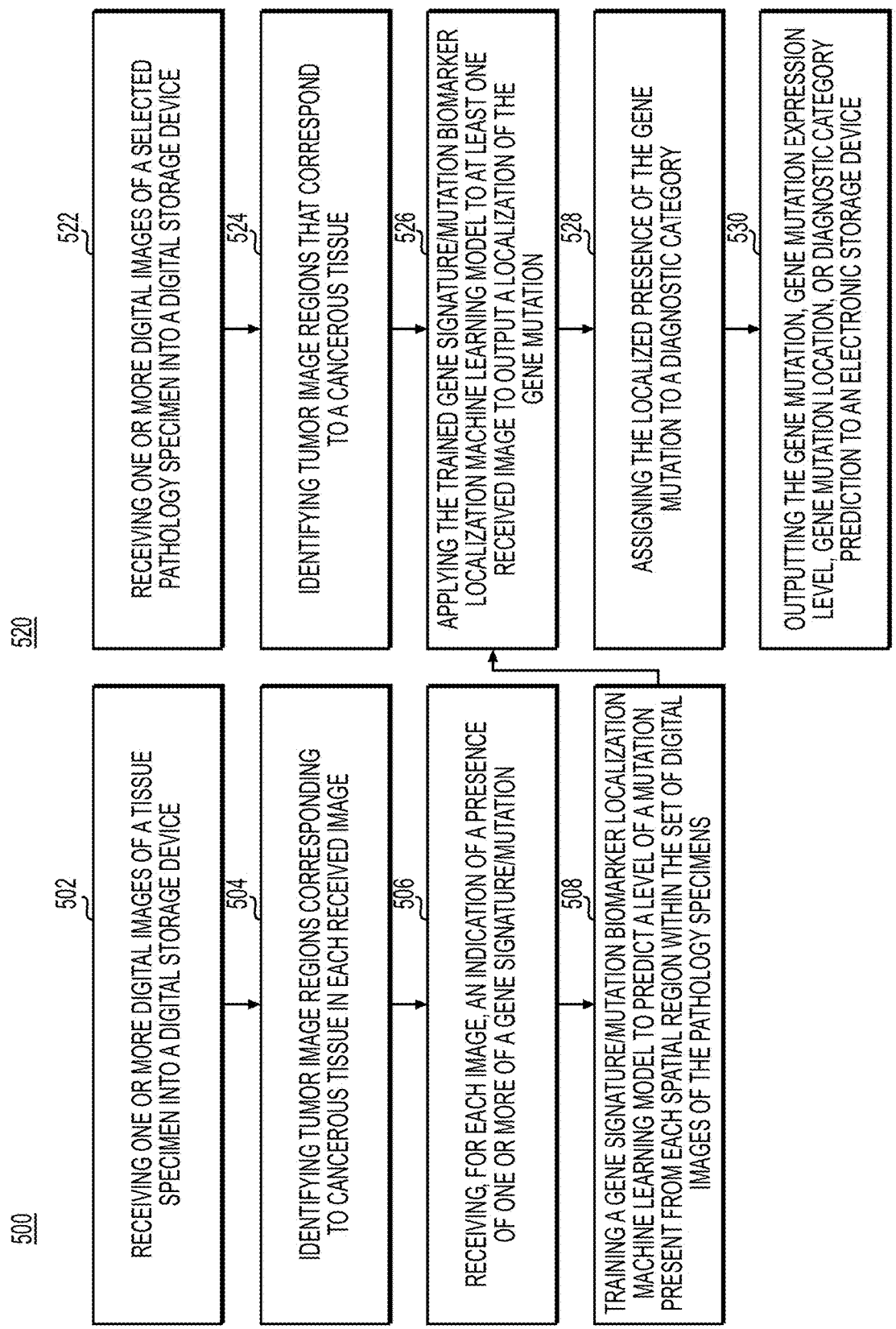
FIG. 5 is a flowchart illustrating an exemplary method for training and using a machine learning model for localization of gene signatures and/or mutations in pathology specimens, according to techniques presented herein.

FIG. 5 is a flowchart illustrating an exemplary method of training and using a machine learning model for localization of gene signatures and/or mutations in pathology specimens. Genetic and molecular testing of cancer tissue may allow for precision treatment of solid tumors via targeted therapies. Even though the cost of genome sequencing has substantially decreased over the years, these tests may still be costly, slow, and require substantial amounts of tissue, tissue that may be limited in clinical studies. Furthermore, the tissue architecture and any information about the spatial relationship between different cells may be lost during these tests. This embodiment may infer localized genetic and molecular biomarkers (such as the over-expression of a protein and/or gene product, amplification, mutations of specific genes, etc.) from digital images of pathology specimens. Exemplary methods 500 and 520 (e.g., steps 502-508 and steps 522-530) may be performed by slide analysis tool 101 automatically or in response to a request from a user.

According to one embodiment, the exemplary method 500 for training a machine learning model for localization of gene signatures and/or mutations in pathology specimens may include one or more of the following steps. In step 502, the method may include receiving one or more digital images of a tissue specimen into a digital storage device (e.g., hard drive, network drive, cloud storage, RAM, etc.).

In step 504, the method may include identifying tumor images regions corresponding to cancerous tissue in each received image, using either an AI-based model (e.g., the tumor region detection model) or manual specification.

In step 506, the method may include receiving, for each image, an indication of the presence of one or more of a gene signature or a gene mutation. The presence of the mutations may be identified using validated sequencing methods. The presence of the mutation may be reported as a categorical variable, and its variant allele fraction and cancer cell fraction (e.g., the bioinformatically-inferred percentage of cancer cells in a sample harboring a given mutation) may be reported on a numeric, ordinal, or binary scale. The indication may be assigned to the entire image or image sub-regions (e.g., tumor).

In step 508, the method may include training a gene signature and/or mutation biomarker localization machine learning model to predict a level of a mutation present from each spatial region within the set of digital images of the pathology specimens.

In step 522, the method may include receiving one or more digital images of a selected tissue specimen into a digital storage device (e.g., hard drive, network drive, cloud storage, RAM, etc.).

In step 524, the method may include identifying tumor image regions that correspond to cancerous tissue for the received images, using either an AI-based method (e.g., the tumor detection model) or manual specification.

In step 526, the method may include applying the trained gene signature and/or mutation biomarker localization machine learning model to the image to output a localization of the gene mutation.

In step 528, the method may include assigning the localized presence of the gene mutation to a diagnostic category.

In step 530, the method may include outputting the gene mutation, gene mutation expression level, gene mutation location or diagnostic category prediction to an electronic storage device. The output may comprise using a visual indicator to assert the user (e.g., a pathologist, histology technician, etc.) of the expression levels and location of each gene mutation.

Figure 6:
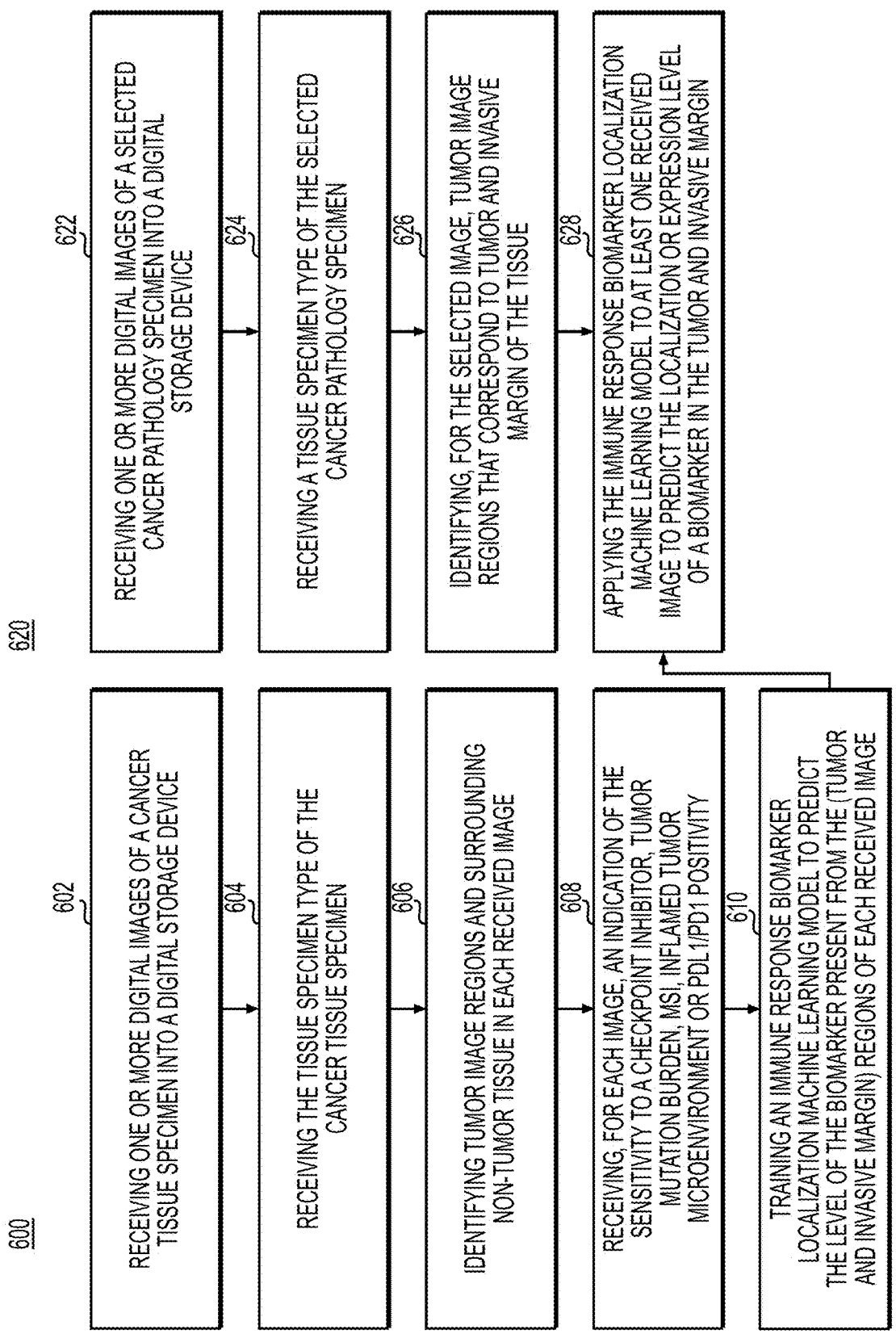
FIG. 6 is a flowchart illustrating an exemplary method for training and using a machine learning model for localization of biomarkers in a tumor microenvironment for immunotherapy response prediction, according to techniques presented herein.

FIG. 6 is a flowchart illustrating an exemplary method of training and using a machine learning model for localization of biomarkers in the tumor microenvironment for immunotherapy response prediction. Recognition of the tumor cells by the immune system for destruction may entail a set of conditions that can be utilized in several biomarkers that are utilized for assessment of the potential efficacy of immunotherapies including antibodies against PD1, PDL1, among others. Some of these biomarkers include the number of somatic mutations (e.g., tumor mutation burden), IHC for markers including MSI (microsatellite instability), PDL1 and PD1, gene expression signatures for the level of inflammation in the microenvironment, among others. In addition to the quantification of the biomarkers, the location of biomarkers with respect to the tumor may also provide critical information in understanding or predicting a therapeutic response.

The embodiment may be used to identify and localize biomarkers in a tumor microenvironment to better understand an immune landscape of patients and their likelihood of responding to immunotherapies. According to the embodiment, the exemplary methods 600 and 620 (e.g., steps 602-610 and steps 622-628) for training a machine learning model for localization of biomarkers in the tumor microenvironment for immunotherapy response prediction may include one or more of the following steps. In step 602, the method may include receiving one or more digital images of a cancer tissue specimen into a digital storage device (e.g., hard drive, network drive, cloud storage, RAM, etc.). For each received image, the method may also include receiving an indication of the presence or absence of the tumor region, e.g., cancerous tissue.

In step 604, the method may include receiving the tissue specimen type of the cancer tissue specimen.

In step 606, the method may include identifying tumor image regions that correspond to tumor and surrounding non-tumor tissue using either an AI-based method (e.g., the tumor region detection model) or manual specification.

In step 608, the method may include receiving, for each image, an indication of the sensitivity to a checkpoint inhibitor, tumor mutation burden, MSI inflamed tumor microenvironment or PDL1/PD1 positivity. These presences may be reported in a categorical scale (e.g., present vs. absent). The indication may be assigned to the entire image or image sub-regions.

In step 610, the method may include training an immune response biomarker localization machine learning model to predict the level of the biomarker present from the (tumor and invasive margin) regions of each received image.

In step 622, the method may include receiving one or more digital images of a selected cancer pathology specimen into a digital storage device (e.g., hard drive, network drive, cloud storage, RAM, etc.).

In step 624, the method may include receiving a tissue specimen type of the selected cancer pathology specimen.

In step 626, the method may include identifying, for the selected image, tumor image regions that correspond to tumor and invasive margin of the tissue using either an AI-based method (e.g., the tumor region detection model) or manual.

In step 628, the method may include applying the immune response biomarker localization machine learning model to at least one received image to predict the localization or expression level of a biomarker in the tumor and invasive margin. The machine learning model may include the following steps:

a. Assigning the presence of a biomarker to a diagnostic category b. Outputting the predicted localization or expression levels of the biomarker to an electronic storage device c. Generating a visual indicator to alert the user (e.g., a pathologist, histology technician, etc.) of the predicted expression levels of the biomarkers.

Figure 7:
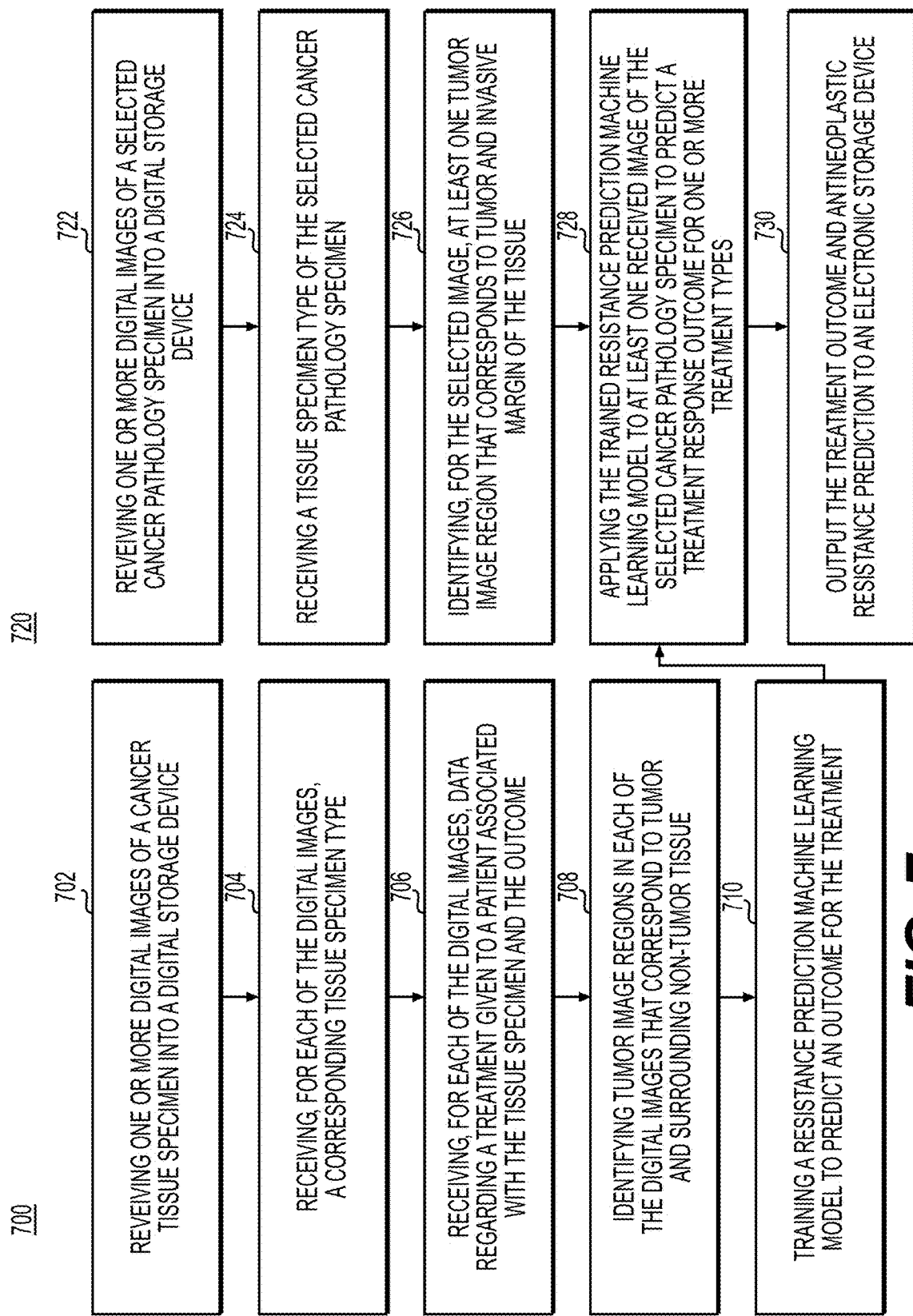
FIG. 7 is a flowchart illustrating an exemplary method for training and using a machine learning model to predict antineoplastic resistance, according to techniques presented herein.

FIG. 7 is a flowchart illustrating an exemplary method of using machine learning to predict antineoplastic resistance, according to an exemplary embodiment of the present disclosure. Antineoplastic resistance may occur when cancer cells resist and survive despite anti-cancer treatments. This ability may evolve in cancers during the course of treatment, and predicting which therapies the cancer will have the most difficulty acquiring resistance to may improve patient treatment and survival. Some cancers may develop resistance to multiple drugs over the course of treatment. The present embodiment may predict the probability of antineoplastic resistance by examining the environment within and external to a tumor.

According to one embodiment, the exemplary method 700 for training an antineoplastic resistance prediction system using AI may include one or more of the following steps. In step 702, the method may include receiving one or more digital images of a cancer tissue specimen (e.g., stained with H&E) into a digital storage device (e.g., hard drive, network drive, cloud storage, RAM, etc.).

In step 704, the method may include receiving, for each of the digital images, a corresponding tissue specimen type.

In step 706, the method may include receiving, for each of the digital images, data regarding a treatment given to a patient associated with the tissue specimen and the outcome (e.g., whether antineoplastic resistance occurred). Exemplary outcomes can be at one time point or multiple time points.

In step 708, the method may include identifying tumor image regions in each of the digital images that correspond to tumor and surrounding non-tumor tissue, using either an AI-based method (e.g., the tumor region detection model) or manual specification.

In step 710, the method may include training a resistance prediction machine learning model, e.g., a deep neural network, to predict an outcome for the treatment (e.g., if antineoplastic resistance developed). This classification may be done using a multi-class or multi-label approach, with treatments that were not given handled as missing values.

Method 720 may be implemented when using the trained system in production. In step 722, the method may include receiving one or more digital images of a selected cancer pathology specimen into a digital storage device (e.g., hard drive, network drive, cloud storage, RAM, etc.).

In step 724, the method may include receiving a tissue specimen type of the selected cancer pathology specimen.

In step 726, the method may include identifying, for the selected image, at least one tumor region that corresponds to tumor and invasive margin of the tissue, using either an AI-based method (e.g., the tumor region detection model) or manual specification.

In step 728, the method may include applying the trained resistance prediction machine learning model to at least one received image of the selected cancer pathology specimen to predict a treatment response outcome for one or more treatment types. The prediction may include whether any antineoplastic resistance will occur to each treatment type.

In step 730, the method may include outputting the treatment outcome and antineoplastic resistance prediction to an electronic storage device. The output may be in the form of a visual indicator to alert the user (e.g., a pathologist, histology technician, etc.) of the treatments that are predicted to be ineffective due to antineoplastic resistance developing. The output may further include recommending treatments based on the predictions, and outputting the treatments to the user or to an electronic storage device.

Figure 8:
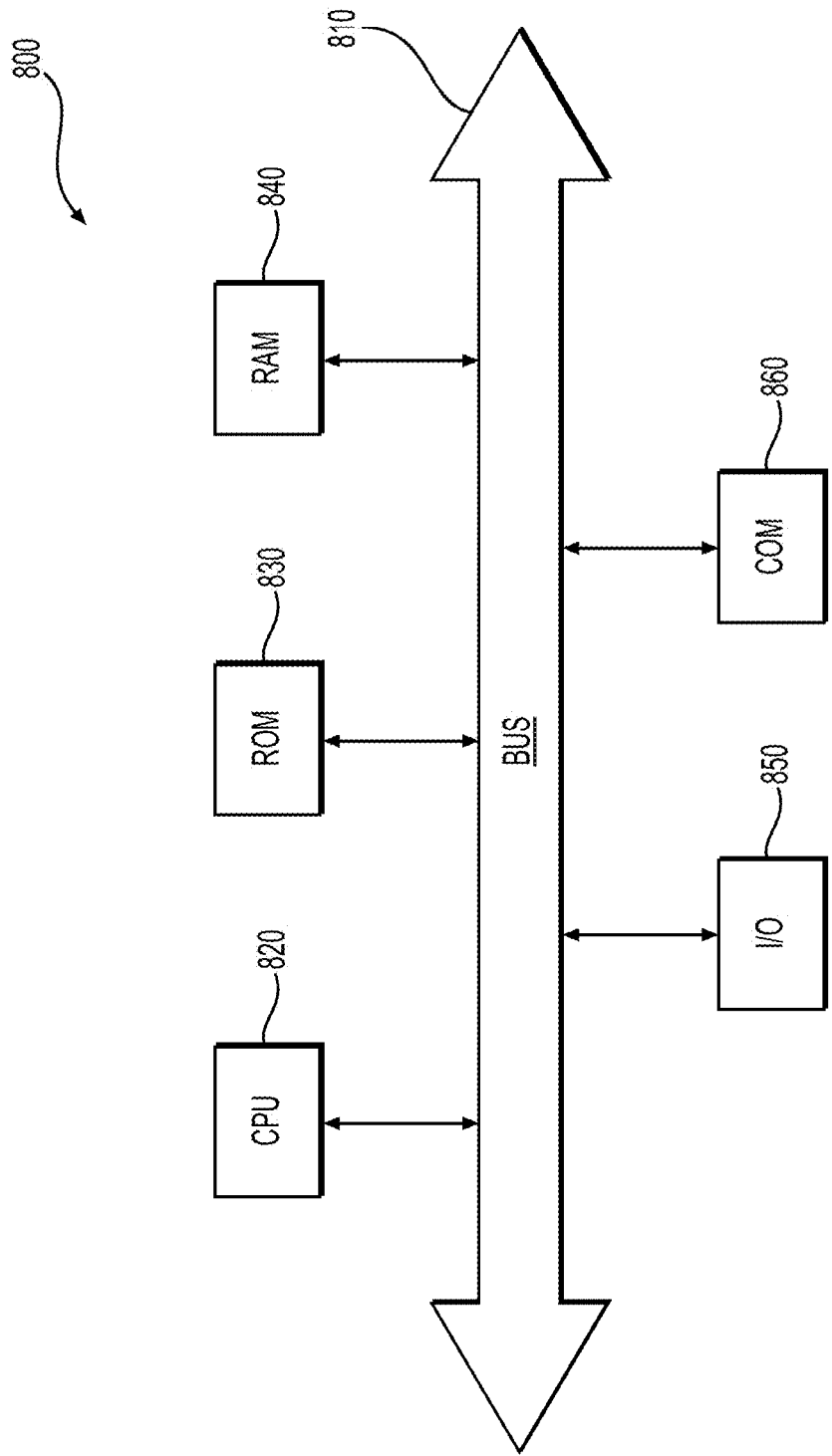
FIG. 8 depicts an example system that may execute techniques presented herein.

As shown in FIG. 8, device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multi-processor system, such system operating alone, or in a cluster of computing devices operating in a cluster or server farm. CPU 820 may be connected to a data communication infrastructure 810, for example, a bus, message queue, network, or multi-core message-passing scheme.

Device 800 also may include a main memory 840, for example, random access memory (RAM), and also may include a secondary memory 830. Secondary memory 830, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include other similar means for allowing computer programs or other instructions to be loaded into device 800. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical, or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 800 also may include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware.

The tools, modules, and functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples be considered as exemplary only.

What is claimed is:

1. A computer-implemented method for analyzing an image corresponding to a specimen, the method comprising:
   receiving one or more digital images of a pathology specimen from a patient, the pathology specimen comprising tumor tissue, the one or more digital images being associated with data about a plurality of biomarkers in the tumor tissue and data about a surrounding invasive margin region around the tumor tissue;
   identifying the tumor tissue and the surrounding invasive margin region for each of the one or more digital images;
   generating, using a machine learning model on the one or more digital images, at least one inference of a presence of the plurality of biomarkers in the tumor tissue and the surrounding invasive margin region;
   determining a spatial relationship of each of the plurality of biomarkers identified in the tumor tissue and the surrounding invasive margin region to themselves and to other cell types;
   training the machine learning model to compare the at least one biomarker and the spatial relationship by receiving at least one spatially structured training input, receiving metadata corresponding to each spatially structured training input, and training the machine learning model to predict a treatment outcome or a resistance prediction from a localized biomarker; and
   determining, based on the spatial relationship of each of the plurality of biomarkers to themselves and to other cell types, a prediction for a treatment outcome and/or at least one treatment recommendation for the patient.

2. The computer-implemented method of claim 1, wherein generating the at least one inference of the presence of the plurality of biomarkers further comprises using a computer vision model.

3. The computer-implemented method of claim 1, wherein the pathology specimen comprises a histology and/or cytology specimen.

4. The computer-implemented method of claim 1, wherein the data about the plurality of biomarkers is identified from genetic testing, flow cytometry, and/or immunohistochemistry.

5. The computer-implemented method of claim 1, wherein identifying the tumor tissue and the surrounding invasive margin region uses the machine learning model, and wherein training the machine learning model further comprises:
   receiving one or more training digital images associated with a training pathology specimen and an associated indication of a presence or an absence of a tumor region;
   dividing the one or more training digital images into at least one sub-region to determine if the tumor is present in the at least one sub-region; and
   training the machine learning model that takes, as an input, one of the one or more training digital images associated with the pathology specimen and predicts whether the tumor is present or not.

6. The computer-implemented method of claim 5, wherein training the machine learning model further comprises:
   receiving one or more digital images associated with a target pathology specimen and an associated indication of a presence or an absence of a tumor region;
   dividing the one or more digital images into at least one sub-region to analyze to determine if the tumor is present in the at least one sub-region;
   applying the machine learning model to one of the one or more digital images to predict which regions of the digital image show a tumor tissue or an invasive margin and could exhibit a biomarker of interest; and
   indicating and flagging a location of at least one tumor region.

7. The computer-implemented method of claim 1, further comprising training the machine learning model to generate the at least one inference of the presence of the plurality of biomarkers comprises:
   receiving one or more training digital images of the pathology specimen;
   receiving a plurality of data on a level of the biomarker present in a tumor and/or an invasive margin region shown in one of the one or more training digital images;
   dividing one of the one or more training digital images into at least one sub-region to determine at least one property for the at least one sub-region;
   identifying at least one tumor and/or at least one invasive margin region relevant to a biomarker of interest; and
   training a machine learning system to predict an expression level of each biomarker from the at least one tumor and/or the at least one invasive margin region.

8. The computer-implemented method of claim 1, wherein generating the at least one inference comprises:
   determining at least one region of interest in the tumor tissue and the surrounding invasive margin region; and
   applying the machine learning model to determine a prediction of a biomarker expression level in the at least one region of interest.

9. The computer-implemented method of claim 1, wherein generating the at least one inference further comprises:
   receiving a spatially structured input;
   receiving metadata corresponding to the spatially structured input; and
   applying the machine learning model to predict the treatment outcome or a resistance prediction from a localized biomarker.

10. A system for analyzing an image corresponding to a specimen, the system comprising:
    at least one memory storing instructions; and
    at least one processor configured to execute the instructions to perform operations comprising:
    receiving one or more digital images of a pathology specimen from a patient, the pathology specimen comprising tumor tissue, the one or more digital images being associated with data about a plurality of biomarkers in the tumor tissue and data about a surrounding invasive margin region around the tumor tissue;
    identifying the tumor tissue and the surrounding invasive margin region for each of the one or more digital images;
    generating, using a machine learning model on the one or more digital images, at least one inference of a presence of the plurality of biomarkers in the tumor tissue and the surrounding invasive margin region by receiving a spatially structured input, receiving metadata corresponding to the spatially structured input, and applying the machine learning model to predict a treatment outcome or a resistance prediction from a localized biomarker;

determining a spatial relationship of each of the plurality of biomarkers identified in the tumor tissue and the surrounding invasive margin region to themselves and to other cell types; and determining, based on the spatial relationship of each of the plurality of biomarkers to themselves and to other cell types, a prediction for a treatment outcome and/or at least one treatment recommendation for the patient.

11. The system of claim 10, wherein generating the at least one inference of the presence of the plurality of biomarkers further comprises using a computer vision model.

12. The system of claim 10, wherein the pathology specimen comprises a histology and/or cytology specimen.

13. The system of claim 10, wherein the data about the plurality of biomarkers is identified from genetic testing, flow cytometry, and/or immunohistochemistry.

14. The system of claim 10, wherein identifying the tumor tissue and the surrounding invasive margin region uses the machine learning model, and wherein training the machine learning model further comprises:
   receiving one or more training digital images associated with a training pathology specimen and an associated indication of a presence or an absence of a tumor region;
   dividing the one or more training digital images into at least one sub-region to determine if the tumor is present in the at least one sub-region; and
   training the machine learning model that takes, as an input, one of the one or more training digital images associated with the pathology specimen and predicts whether the tumor is present or not.

15. The system of claim 14, wherein training the machine learning model further comprises:
   receiving one or more digital images associated with a target pathology specimen and an associated indication of a presence or an absence of a tumor region;
   dividing the one or more digital images into at least one sub-region to analyze to determine if the tumor is present in the at least one sub-region;
   applying the machine learning model to one of the one or more digital images to predict which regions of the digital image show a tumor tissue or an invasive margin and could exhibit a biomarker of interest; and
   indicating and flagging a location of at least one tumor region.

16. The system of claim 10, further comprising training the machine learning model to generate the at least one inference of the presence of the plurality of biomarkers comprises:
   receiving one or more training digital images of the pathology specimen;
   receiving a plurality of data on a level of the biomarker present in a tumor and/or an invasive margin region shown in one of the one or more training digital images;
   dividing one of the one or more training digital images into at least one sub-region to determine at least one property for the at least one sub-region;
   identifying at least one tumor and/or at least one invasive margin region relevant to a biomarker of interest; and
   training a machine learning system to predict an expression level of each biomarker from the at least one tumor and/or the at least one invasive margin region.

17. The system of claim 10, wherein generating the at least one inference comprises:
   determining at least one region of interest in the tumor tissue and the surrounding invasive margin region; and
   applying the machine learning model to determine a prediction of a biomarker expression level in the at least one region of interest.

18. The system of claim 10, further comprising:
   training the machine learning model to compare the at least one biomarker and the spatial relationship by:
   receiving at least one spatially structured training input;
   receiving metadata corresponding to each spatially structured training input; and
   training the machine learning model to predict a treatment outcome or a resistance prediction from a localized biomarker.

19. A method for analyzing an image corresponding to a specimen, the method comprising:
   receiving one or more digital images of a pathology specimen from a patient, the pathology specimen comprising tumor tissue, the one or more digital images being associated with data about a plurality of biomarkers in the tumor tissue and data about a surrounding invasive margin region around the tumor tissue;
   identifying the tumor tissue and the surrounding invasive margin region for each of the one or more digital images;
   generating, using a machine learning model on the one or more digital images, at least one inference of a presence of the plurality of biomarkers in the tumor tissue and the surrounding invasive margin region by receiving a spatially structured input, receiving metadata corresponding to the spatially structured input; and applying the machine learning model to predict a treatment outcome or a resistance prediction from a localized biomarker;
   determining a spatial relationship of each of the plurality of biomarkers identified in the tumor tissue and the surrounding invasive margin region to themselves and to other cell types; and
   determining, based on the spatial relationship of each of the plurality of biomarkers to themselves and to other cell types, a prediction for a treatment outcome and/or at least one treatment recommendation for the patient.

* * * * *